(12) United States Patent
Choi

(10) Patent No.: US 8,188,005 B2
(45) Date of Patent: May 29, 2012

(54) LIQUID COMPOSITION FOR PROMOTING PLANT GROWTH CONTAINING TITANIUM DIOXIDE NANOPARTICLES

(75) Inventor: Kwang-Soo Choi, Wansan-Gu (KR)

(73) Assignee: Kwang-Soo Choi, Jeonju-si, Jeollabuk-do (KR)

( * ) Notice: Subject to any disclaimer, the term of this patent is extended or adjusted under 35 U.S.C. 154(b) by 309 days.

(21) Appl. No.: 12/714,117

(22) Filed: Feb. 26, 2010

(65) Prior Publication Data

US 2010/0160161 A1 Jun. 24, 2010

Related U.S. Application Data

(63) Continuation-in-part of application No. 10/500,069, filed on Jun. 25, 2004, now abandoned.

(30) Foreign Application Priority Data

Jan. 15, 2002 (KR) .............................. 2002-0002388

(51) Int. Cl.
*A01N 59/16* (2006.01)
*C08F 4/64* (2006.01)

(52) U.S. Cl. ............ 504/120; 71/31; 502/102; 502/218; 502/227

(58) Field of Classification Search ...... 71/31; 502/102, 502/218, 227
See application file for complete search history.

(56) References Cited

U.S. PATENT DOCUMENTS

| 4,525,204 | A | 6/1985 | Holmwood et al. |
|---|---|---|---|
| 4,588,433 | A | 5/1986 | Schmitt et al. |
| 6,093,681 | A | 7/2000 | Ward et al. |
| 6,132,745 | A | 10/2000 | Marchi-Lemann et al. |
| 6,174,840 | B1 | 1/2001 | Pauson et al. |
| 6,235,683 | B1 | 5/2001 | Glenn et al. |
| 6,589,912 | B2 | 7/2003 | Kawai |
| 6,630,172 | B2 | 10/2003 | Batarseh |
| 6,905,814 | B1 | 6/2005 | Aubay et al. |
| 2003/0013369 | A1 | 1/2003 | Soane et al. |

FOREIGN PATENT DOCUMENTS

| KR | 10-2000-0010192 | 2/2000 |
|---|---|---|
| KR | 10-2001-0041042 | 5/2001 |
| KR | 10-2001-0041045 | 5/2001 |

*Primary Examiner* — Gina C Yu
(74) *Attorney, Agent, or Firm* — Sherr & Vaughn, PLLC

(57) ABSTRACT

Disclosed herein is a liquid composition for promoting plant growth containing titanium dioxide nanoparticles. The liquid composition contains, as an active ingredient, an aqueous solution prepared by adjusting the pH of colloidal titanium dioxide, a plant growth promoting component, to 0.4-0.6, in order to prevent rapid precipitation of the colloidal titanium dioxide, and then diluting the colloidal titanium dioxide with water to a predetermined concentration. The colloidal titanium dioxide, an environmentally friendly substance harmless to plants and the human body, which is contained in the plant growth promoting composition, is prevented from rapidly precipitating when it is diluted for application to plants. The plant growth promoting composition is harmless to organisms, reduces environmental contamination caused by over-application of biochemical fertilizers and is inexpensive, leading to an increase in farmer's income.

12 Claims, 2 Drawing Sheets

LIQUID COMPOSITION FOR PROMOTING PLANT GROWTH CONTAINING TITANIUM DIOXIDE NANOPARTICLES

BACKGROUND OF THE INVENTION

1. Field of the Invention

The present invention relates to a liquid composition for promoting plant growth, which contains titanium dioxide nanoparticles. More particularly, the present invention relates to a liquid composition for promoting plant growth, which contains colloidal titanium dioxide, wherein the colloidal titanium dioxide is prevented from rapidly precipitating, such that it can be absorbed by plant foliage to provide light energy directly to plants, thereby promoting plant photosynthesis and growth, thereby significantly increasing crop yield.

2. Description of the Prior Art

Currently, the problem to be solved in the agricultural field is to minimize land devastation and environmental contamination caused by over-application of various chemicals used for the increased production of foods.

Methods for promoting plant growth according to the prior art can be broadly divided into two categories.

A first method which utilizes chemical fertilizers temporarily seems to be effective, but ultimately deteriorates the conditions of the soil in which plants grow. Thus, a vicious circle arises in that fertilizers must be applied again in order to improve the deteriorated soil conditions. As a result, this method is not preferred in a long-term view.

A second method utilizes plant growth regulators which are plant extracts or similar substances which are artificially synthesized.

A method is known which utilizes N-acylalanine derivatives, indole acetic acid, gibberellin, benzylaminopurine, indolebutyric acid, or mixtures thereof. However, this method is expensive and has a handling problem in that an alcohol solvent must be used. Also, this has a shortcoming of causing chemical damage to plants.

Moreover, the use of these substances provides some growth promoting effects, but shows side effects and inevitably involves a damage caused by the improper use of chemicals.

Plants must adapt to the surrounding environment in order to regulate the in vivo metabolism. Nevertheless, the method limited only to the growth of plants results in a reduction in productivity and even killing of plants.

Meanwhile, Korean Patent Registration No. 10-0287525 (entitled "Plant Growth Promoter") discloses a plant growth promoter which utilizes 2-methyl-4-dimethylaminomethyl-5-hydroxybenzimidazole, thereby inhibiting mutation, preventing oxidation and increasing resistance to disease.

The above chemical fertilizer and the plant growth promoter consist mostly of artificially synthesized organic substances which have various components. Thus, even when the same substance is used, results varying depending on the condition of use are obtained.

Recently, there was an attempt to substitute the chemical fertilizer with natural inorganic substances containing composite ingredients. However, this shows an insufficient effect while it seems that much damage will be caused by heavy metals contained therein.

Accordingly, new plant growth promoters which use the functions of known natural substances have been developed as follows.

Japanese Patent Application Laid-Open No. 2001-10914 (entitled "Composition for foliar application and use thereof) discloses a composition for application to plant foliage which contains a titanium dioxide semiconductor photocatalyst.

The composition for application to plant foliage is prepared for the purpose of applying titanium oxide to plants, but in order to apply titanium oxide to plants, colloidal titanium oxide nanoparticles are used, after they are diluted a large amount of water and mixed with substances such as fertilizers or agricultural chemicals.

In this case, however, even colloidal titanium dioxide nanoparticles with ensured dispersibility undergo pH shock when diluted in water, such that they rapidly precipitate. Thus, even if they are used mixed with other substances, they will not substantially assist in plant growth.

SUMMARY OF THE INVENTION

Accordingly, the present invention has been made in view of the problems occurring in the prior art, and it is an object of the present invention to use colloidal titanium dioxide harmless to plants and the human body, in which the pH of the colloidal titanium oxide is adjusted so as to ensure its dispersion stability, such that they can be smoothly absorbed by plant foliage, thereby significantly increasing the production of crops.

To achieve the above object, the present invention provides a liquid composition for promoting plant growth which contains, as an active ingredient, an aqueous solution prepared by adjusting the pH of colloidal titanium dioxide, a plant growth promoting component, to 0.4-0.6, in order to prevent rapid precipitation of the colloidal titanium dioxide, and then diluting the colloidal titanium dioxide with water to a predetermined concentration.

Preferably, the pH of the colloidal titanium dioxide is adjusted by adding thereto an inorganic acid together with one or two selected from the group consisting of an organic acid, having a hydroxyl group (—OH) and a carboxyl group (—COOH), and a carbon-based amino acid having a hydroxyl group (—OH), an amino group (—$NH_2$) and a carboxyl group (—COOH) as polar functional groups.

The aqueous solution may be neutralized by further adding thereto at least one alkaline substance selected from the group consisting of alkali metal hydroxides, including sodium hydroxide (NaOH), potassium hydroxide (KOH) and lithium hydroxide (LiOH), ammonium hydroxide ($NH_4OH$), trimethylamine (($CH_3$)$_3$N) and triethylamine (($C_2H_5$)$_3$N).

DETAILED DESCRIPTION OF THE INVENTION

Figure 1:
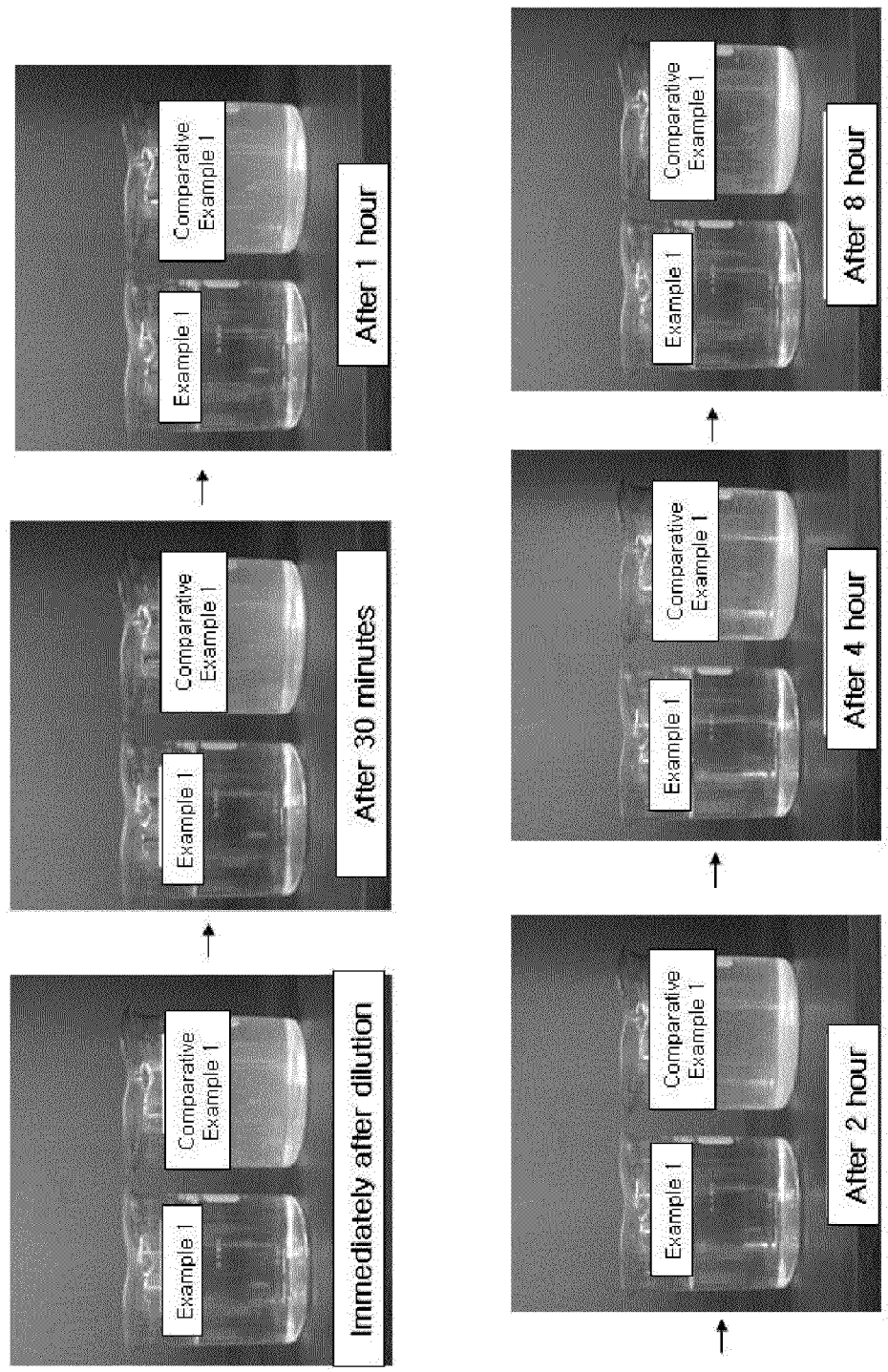
FIG. 1 shows the degree of precipitation of a composition for promoting plant growth according to the present invention as a function of time.

The present invention relates a liquid composition for promoting plant growth which contains titanium oxide nanoparticles.

The present invention has been made by finding a novel substance which promotes the growth and metabolism of plants and at the same time, does not cause a problem of environmental contamination, and conducting a test for applying the novel substance to plants.

Factors necessary for plant growth include nutrients, water, temperature, light and the like.

Plant growth is determined by the amount of the most deficient inorganic element according to the law of minimum nutrient, when other conditions are the same.

Although optimizing the feed rate of inorganic elements for each of various plants is necessary, it is actually difficult since either the conditions of the soil in which plants grow or the surrounding environmental conditions vary.

Therefore, deviating from the conventional formality of combinations of organic fertilizers with inorganic elements, the present inventors have made an attempt to find a novel substance which has not been used hitherto.

On the basis of the fact that plants grow while obtaining the nutrients from the substances synthesized by photosynthesis based on solar energy, the present inventors have attempted to find the substances capable of utilizing solar energy.

The present inventors have found photocatalytic titanium dioxide ($TiO_2$) as a substance consistent with the above object, which has a guaranteed safety for the human body and plants, and functionalities including sterilization and decomposition of poisonous organisms, and is formed of easily available materials, thereby completing the present invention.

As used herein, the term "photocatalyst" refers to a substance which helps a chemical reaction to occur by absorbing light of a necessary wavelength range from sunlight or artificial illumination.

Such a photocatalytic substance has a function of oxidizing poisonous substances into carbon dioxide ($CO_2$) and water ($H_2O$) using oxygen ($O_2$) and water ($H_2O$) as oxidizing agents under light irradiation.

Also, titanium dioxide has recently been highlighted as a photocatalyst, since it has advantages in that it is relatively inexpensive, not photodecomposed, can be used in a semi-permanent manner and does not cause a problem of environmental contamination. Based on this point, the present inventors have discovered a manner of applying photocatalytic titanium dioxide directly to plants.

However, conventional photocatalytic titanium dioxide has a pH of less than 2, and thus even if it is prepared in a colloidal form and used as a composition for promoting plant growth, the storage stability thereof will be reduced due to rapid precipitation. Also, if an alkaline substance is added thereto for neutralization, the precipitation of the colloidal titanium dioxide will occur due to pH shock, and even if a dispersion stabilizer is added thereto, the colloidal titanium dioxide will lose its dispersion stability when it is diluted in a large amount of water.

For these reasons, in the present invention, in order to prepare a composition for promoting plant growth having dispersion stability, the pH of colloidal titanium dioxide is adjusted to 0.4-0.6, such that the colloidal titanium dioxide is prevented from rapidly precipitating and, at the same time, does not precipitate even when it is mixed with other components such as fertilizers. Thus, when the inventive composition containing the colloidal titanium dioxide is applied to a plant, it can show the effect of promoting the growth of the plant.

More specifically, because titanium dioxide generally has an isoelectric point of about pH 4, it is kept in a stable colloidal form in the acidic and alkaline regions.

However, if the colloidal titanium dioxide is diluted with water, the pH thereof will be closer to the isoelectric point as the dilution ratio increases, and the colloidal titanium dioxide will ultimately change into a precipitate.

Accordingly, the preset inventors have found that, when a composition prepared by adjusting the pH of colloidal titanium dioxide to 0.4-0.6 in order to prevent it from rapidly precipitating after dilution, and then diluting the colloidal titanium dioxide with water, is applied to plant foliage, the titanium dioxide will be mostly absorbed into the plant to show the effect of promoting plant growth, because it does not precipitate after dilution.

Herein, the adjustment of pH is preferably performed using an inorganic acid together with one or two selected from the group consisting of organic acids, having a hydroxyl group (—OH) and a carboxyl group (—COOH), and carbon-based amino acids having a hydroxyl group (—OH), an amino group (—$NH_2$) or a carboxyl group (—COOH) as polar functional groups. When the range of pH adjusted is 0.4-0.6, the dispersion stability of the colloidal titanium dioxide can be obtained, such that the colloidal titanium dioxide is prevented from rapidly precipitating, and thus has the greatest effect on plant growth.

The inorganic acid which is used in the present invention is one selected from the group consisting of hydrogen chloride, hydrogen bromide, hydrogen iodide, nitric acid, sulfuric acid and perchloric acid and serves as a pH adjusting agent in the present invention.

The amino acid which is used in the present invention is an organic acid having both an amino group (—$NH_2$) and a carboxylic group (—COOH) in one molecule and serves an agent for preventing pH shock.

The amino acid is α-amino acid in which the amino group and the carboxyl group are linked to the same carbon atom. Thus, it can be represented by a formula of R—$CHNH_2$—COOH wherein R represents an aliphatic, aromatic or heterocyclic substituent.

Amino acids constituting proteins, excluding glycine, all have stereoisomers isomers. The amino acids in the proteins have the same configuration of amino group and carboxyl group with respect to the α-carbon atom and are present in the L-form in vivo.

By a chemical synthesis method, the DL-racemic form containing the D-form and the L-form in the same amount can be obtained.

Meanwhile, the amino acids are classified, according to the characteristic of R, into basic amino acids such as glycine, alanine, valnine, leucine or isoleucine, aromatic amino acids such as phenyl-alanine or tyrosine, sulfur-containing amino acids such as methionine or cysteine, oxyamino acids such as serine or threonine, and heterocyclic amino acids such as histidine or tryptophane.

Among the amino acids, the oxyamino acids such as serine or threonine belong to carbon compounds having a hydroxyl group (—OH), an amino group (—$NH_2$) and a carboxyl group (—COOH) as polar functional groups.

Thus, it can be seen that, when the amino acid is used to prepare the inventive composition for promoting plant growth, it makes it possible to prepare a composition which is stable without agglomeration of the titanium dioxide particles, and when the composition is mixed with various fertilizer components, agglomeration of these fertilizer components with the titanium dioxide can be inhibited to improve the dispersion stability of the titanium dioxide, and thus, the inventive composition has the effect of promoting plant growth.

The present inventors have found that, even when the plant growth promoting composition prepared as described above contains a high concentration of titanium dioxide and is stored for a long period of time, it will show no precipitation and thus can be stored for a long period of time, and found that, even if various fertilizer components are added to the composition, problems associated with compatibility will not occur. Based on these findings, the present inventors have prepared the plant growth promoting composition.

Also, it can be seen that the organic acid, a carbon compound having no amino group but having both a hydroxyl group and a carboxyl group in the carbon atom, may also be used as a pH shock preventing agent in the present invention.

Herein, the organic acid preferably has not more than 7 carbon atoms.

If the organic acid has more than 8 carbon atoms, the solubility thereof in water will be reduced, so that the effect of protecting titanium dioxide from precipitation will be reduced. Thus, in this case, when the titanium dioxide is diluted in a large amount of water or mixed with fertilizer components, the titanium dioxide particles will be agglomerated.

Specifically, examples of organic acids which can be used in the present invention include glycolic acid ($HOCH_2COOH$) as a $C_2$ organic acid, lactic acid ($CH_3CH(OH)COOH$) as a $C_3$ organic acid, malic acid ($HOOCCH(OH)CH_2COOH$) as a $C_4$ organic acid, tartaric acid ($HOOCCH(OH)CH(OH)COOH$) as a $C_5$ organic acid, and citric acid ($HOC(CH_2COOH)_2COOH$) or gluconic acid ($HOCH_2(CHOH)_4COOH$) as $C_6$ organic acid.

An organic acid in which the hydroxyl group and the carboxyl group are not present on the same carbon atom is not suitable for the object of the present invention, because it provides insufficient protection against pH shock and various ion species.

In other words, salicylic acid ($HOC_6H_4COOH$), a kind of β-hydroxyl acid, 3-hydroxybutyric acid ($CH_3CH(OH)CH_2COOH$) and the like, when adjusted to a pH of more than 5 and mixed with fertilizer components, cannot effectively prevent agglomeration of the titanium dioxide particles.

Also, multivalent carboxylic acids such as succinic acid ($HOOCCH_2CH_2COOH$) or adipic acid ($HOOCCH_2CH_2CH_2CH_2COOH$), which are carbon compounds having more than two carboxyl groups without a hydroxyl group, when adjusted to a pH of more than 5 and mixed with fertilizer components, cannot effectively prevent agglomeration of the titanium dioxide particles.

Accordingly, in the present invention, at least one organic acid selected from the group consisting of glycolic acid, lactic acid, citric acid, tartaric acid, malic acid and gluconic acid, which have a hydroxyl group (—OH) and a carboxyl group (—COOH) as polar functional groups on the same carbon atom, is used to adjust the pH of the colloidal titanium dioxide.

The colloidal titanium dioxide nanoparticles whose pH has been adjusted as described above are diluted with a large amount of water to neutralize the pH thereof or are neutralized by adding at least one alkaline substance selected from the group consisting of alkali metal hydroxides such as sodium hydroxide (NaOH), potassium hydroxide (KOH) or lithium hydroxide (LiOH), ammonium hydroxide ($NH_4OH$), trimethylamine (($CH_3)_3N$) and triethylamine (($C_2H_5)_3N$). In this case, it can be seen that a plant growth promoting composition which is stable without agglomeration of the titanium dioxide particles can be prepared.

Moreover, in the process of preparing the colloidal titanium dioxide, it was observed that the precipitation time of the titanium dioxide was more delayed as the particle size of the titanium dioxide became smaller.

From these results, it was found that titanium dioxide nanoparticles are suitable as the main component of the composition for promoting plant growth and metabolism which is the object of the present invention.

For the above object, a variety of titanium dioxide nanoparticles can be used. Although titanium dioxide nanoparticles having a particle size of 3 to 200 nm have excellent absorption and workability and shows an excellent increase in crop yield, a solution in which fine particles of several tens of microns are dispersed may also be used.

Any titanium dioxide particles may be used whether it is primary particles in a monodispersed state or secondary particles formed by agglomeration of the primary particles, as observed with a scanning electron microscope, as long as the titanium dioxide particles can stably maintain a dispersed state.

Moreover, although the particles of various shapes may be used, it is preferred for the present invention to use the sphere-, needle- or plate-shaped titanium dioxide nanoparticles.

Meanwhile, although the crystal structure of titanium dioxide used for the above purpose may be anatase-type, rutile-type, brookite-type or a mixture thereof, the anatase-type crystal structure is particularly preferred.

The anatase-type crystal structure is excited by absorbing near-ultraviolet light of about 380 nm from sunlight and, at the same time, exhibits strong oxidation power by separation of electrons from holes such that it decomposes most of poisonous organisms. For this reason, it is believed to be a crystal structure which is most consistent with the above object.

When the colloidal titanium dioxide is diluted with water and applied to crops, the dilution factor will have a great effect on crop yield.

In the present invention, the concentration of titanium dioxide nanoparticles after final dilution is 1 to 1,000 ppm, preferably 3 to 300 ppm and more preferably 3 to 150 ppm.

If the concentration is above 1,000 ppm, costs will be increased while the possibility of causing chemical injury to plants will be rather increased. If the concentration is below 1 ppm, the effect of the titanium dioxide nanoparticles will be rapidly reduced.

Since the colloidal titanium dioxide solution when applied to the foliage of crops shows the highest increase in crop yield, it basically differs from the existing soil conditioners.

Since the titanium dioxide nanoparticle which is the main component of the composition according to the present invention acts to highly increase the crop yield by itself, it shows a sufficient growth promoting effect without needing to add separate assistant additives. However, it is obvious to those skilled in the art that fertilizer ingredients necessary for the growth of plants, other metallic or non-metallic oxides, or surfactants serving as an absorber or a spreader, may be added.

In other words, the titanium dioxide nanoparticles are contained in order to promote photosynthesis, and since the assistant additives are added as stabilizers and enhancers in order to further increase the yield of crops, they may be added to the plant growth promoting composition of the present invention.

Oxides of Li, Be, B, Na, Mg, Al, Si, P, K, Ca, Sc, V, Cr, Mn, Fe, Co, Ni, Cu, Zn, Ga, Ge, Se, Zr, or mixtures thereof, may be used as the fertilizer ingredients or metallic or non-metallic oxides. Furthermore, carbonates, chlorides, nitrates or sulfates of the above elements may also be used, as long as the materials containing the above elements are dissolved in water and can be absorbed by plants.

The amount of metallic or non-metallic oxides added is 0.1 to 20% by weight, and preferably 0.5 to 15% by weight, relative to the titanium dioxide solids that are the main components of the liquid composition according to the present invention.

A bactericidal effect shown by the titanium dioxide nanoparticle solution is attributable to the oxidizing power of the semiconductor which occurs when the semiconductor is exposed directly or indirectly exposed to sunlight. For this reason, under the condition having the blocking of sunlight or the nighttime having little or no radiation of sunlight, the bactericidal effect will be deteriorated.

Based on this point, the present inventors have found that silver (Ag) nanoparticles having the ability to kill phytopathogenic bacteria by contacting directly with the phytopathogenic bacteria can be used as another assistant additive.

Generally, silver nanoparticles having a particle size of 1 to 100 nm are stably dispersed in an aqueous solution. If the silver nanoparticles, after added to the titanium dioxide solution, are applied, the ability of the titanium dioxide is then further increased due to high bactericidal activity of the silver nanoparticles. Moreover, the silver nanoparticles which are expensive are difficult to apply to agricultural crops alone, but they are used together with titanium dioxide, they exhibit excellent bactericidal activity even in a very small amount.

Although the amount of silver nanoparticles added may be selected within the range in which cost effectiveness is ensured, the present inventors have found that it is preferably in the range of 0.5 to 20% by weight, and more preferably 1.0 to 10% by weight, relative to the titanium dioxide solids.

In the present invention, examples of surfactants which may be added to the aqueous titanium dioxide solution and used as an absorber or spreader include a cationic surfactant, a nonionic surfactant, an anionic surfactant, and an ampotheric surfactant. The kind of surfactant used in the present invention may vary depending on the kind of plants to which the titanium dioxide solution is applied.

One or two kinds or more of the surfactants as described above are mixed at a suitable ratio and added to the aqueous titanium dioxide solution. In this case, the amount of surfactants is preferably added in an amount of 0.1 to 5% by weight, and more preferably 0.2 to 1% by weight, relative to the weight of the titanium dioxide.

Hereinafter, the method for preparing the plant growth promoting composition of the present invention will be described in detail.

1. Preparation of Liquid Composition for Promoting Plant Growth Containing Titanium Dioxide Nanoparticles 1) Step 1: Preparation of Colloidal Titanium Dioxide Nanoparticles Colloidal titanium dioxide ($TiO_2$) nanoparticles having a particle size of 3-100 nm are prepared.

If the particle size of the titanium dioxide nanoparticles is smaller than 3 nm or larger than 100 nm, the titanium dioxide nanoparticles will be unstable under the influence of gravity to agglomerate and precipitate slowly even when a stabilizer and a dispersing agent are added thereto. For this reason, such titanium dioxide nanoparticles cannot be absorbed by plant foliage when they are applied.

Also, in order to obtain a plant growth promoting effect through the high dispersion stability of the titanium dioxide nanoparticles, a zirconium salt may be added to the titanium dioxide nanoparticles or prepared using an acidic salt included in the titanium dioxide.

The zirconium salt which can be used in the present invention may be one or a mixture of two or more selected from the group consisting of zirconium oxyacetate ($Zr(OH)_2(CH_3COO)_2$), zirconium oxychloride ($ZrOCl_2$) and zirconium oxynitrate ($Zr(NO_3)_2$).

The zirconium salt is preferably used in an amount of 1-15 wt % based on the weight of the colloidal titanium dioxide.

Moreover, the crystal forms of the titanium dioxide nanoparticles include anatase, rurile and brookite, but among the three crystal forms, the anatase crystal form is preferably used, because it has an excellent photocatalytic effect and, at the same time, is cost-effective.

2) Step 2: Preparation of Plant Growth Promoting Composition after pH Adjustment The pH of the prepared colloidal titanium dioxide nanoparticles is adjusted.

Herein, the pH is adjusted by adding an inorganic acid together with one or two selected from organic acids or amino acids.

The inorganic acid which is used in the present invention is one selected from the group consisting of hydrogen chloride, hydrogen bromide, hydrogen iodide, nitric acid, sulfuric acid and perchloric acid.

The amino acid which is used in the present invention is one or two selected from the group consisting of serine and threonine, which have a hydroxyl group (—OH), an amino group ($NH_2$) and a carboxyl group (—COOH) as polar functional groups.

The organic acid which is used in the present invention is one or a mixture of two or more selected from the group consisting of glycolic acid, lactic acid, citric acid, tartaric acid, malic acid and gluconic acid, which have a hydroxyl group (—OH) and a carboxyl group (—COOH) as polar functional groups on the same carbon atom.

Among the above organic acids, the use of citric acid can provide the greatest effect, because it can further increase the storage stability of the plant growth promoting composition of the present invention.

Also, in the present invention, the amino acid and the organic acid are added based on the amount of the solid titanium dioxide which is used as a main material for preparing the colloidal titanium dioxide nanoparticles. Thus, one or two substances selected from among the amino acids and the organic acids are preferably added in an amount of 10-300 g per 100 of the solid titanium dioxide nanoparticles which are contained in the colloidal titanium dioxide nanoparticles.

If one or two acids selected from among the amino acids and the organic acids are added in an amount smaller than 10 g, the function of protecting the colloidal titanium dioxide against pH shock will be reduced, partial agglomeration of the titanium dioxide nanoparticles may occur in the process of adding and mixing the acids. On the other hand, if the acids are added in an amount larger than 300 g, they will not increase the function of protecting the colloidal titanium dioxide against pH shock and will be disadvantageous in terms of cost.

Moreover, the amino acid or the organic acid may be used directly without any further treatment, and a salt thereof, such as a sodium, potassium or calcium salt, may also be used.

If the salt is used, the amount of alkaline substance added in the process of adjusting the pH of the colloidal titanium dioxide can be reduced.

Examples of the salt which can be used in the present invention include sodium lactate ($CH_3CH(OH)COONa$), calcium lactate ($[CH_3CH(OH)COO]_2Ca$) sodium malate ($NaCOOCH(OH)CH2COONa_2$), disodium L-tartarte, trisodium citrate ($HOC(CH_2COO)_2COONa_3$), tripotassium citrate ($[HOC(CH_2COO)_2COO]_2Ca_3$) and the like.

The colloidal aqueous solution of titanium dioxide ($TiO_2$) nanoparticles subjected to the above-described process is neutralized by dilution with a large amount of water before use.

Alternatively, the colloidal aqueous solution may be neutralized by adding an alkaline substance. In the present invention, because the colloidal titanium dioxide nanoparticles are in the state in which the dispersion stability was already increased, the precipitation of the titanium dioxide nanoparticles does not occur even when the alkaline substance is added. Thus, when the colloidal titanium dioxide solution containing the alkaline substance is applied to plant foliage, it can be mostly absorbed by the plant foliage, thus maximizing the effect of promoting plant growth.

The alkaline substance which may be used in the neutralization process as described above is one or a mixture of two or more selected from the group consisting of alkali metal hydroxides such as sodium hydroxide (NaOH), potassium hydroxide (KOH) or lithium hydroxide (LiOH), and alkaline substances such as ammonium hydroxide ($Na_4OH$), trimethylamine ($(CH_3)_3N$) or triethylamine ($(C_2H_5)_3N$).

If the pH of the aqueous colloidal solution of titanium dioxide nanoparticles neutralized with the alkaline substance is less than 5, the dispersion of the titanium dioxide nanoparticles will be insufficient even when a substance of protecting the nanoparticles against pH shock is added, because the pH of the colloidal aqueous solution is close to the isoelectric point of titanium dioxide. If the pH of the aqueous colloidal solution of titanium dioxide nanoparticles is adjusted to more than 12 by continuously adding the alkaline substance, the composition will not change, but it will be difficult to mix with fertilizer components. For these reasons, the aqueous colloidal solution of titanium dioxide nanoparticles is preferably adjusted to a pH of 5-12.

Hereinafter, the present invention will be described in further detail with reference to examples and test examples. It is to be understood, however, that these examples are for illustrative purposes only and are not to be construed to limit the scope of the present invention.

Example 1

Preparation of Liquid Composition for Promoting Plant Growth Containing Titanium Dioxide Nanoparticles As a starting material for titanium dioxide used in the present invention, the organic titanium alkoxide TTIP (titanium tetraisopropoxide; JUNSEI; a solid content of 97%) was used.

240 ml of 70% nitric acid was added to 8.94 liters of deionized water to prepare a mixed solution.

The mixed solution was slowly added dropwise to the TTIP, and then stirred under reflux at 80° C. so as to be hydrolyzed.

After completion of the hydrolytic reaction, a blue colloidal solution of titanium dioxide having a solid content of 2.0 wt % and a pH of 0.7 was obtained.

The crystal structure of the colloidal titanium dioxide nanoparticles was found to be the anatase form as observed by XRD, and more than 95% of the colloidal titanium dioxide nanoparticles were present in the particle size range of 15-25 nm.

The colloidal titanium dioxide solution was adjusted to a pH of 0.5 by adding 300 ml of nitric acid (inorganic acid) and 100 ml of serine (organic acid).

Then, the colloidal titanium dioxide solution was diluted with 7990 liters to a titanium dioxide concentration of 25 ppm, thereby preparing a liquid composition for promoting plant growth according to the present invention.

Comparative Example 1

Preparation of Liquid Composition for Promoting Plant Growth

As a starting material for titanium dioxide used in the present invention, the organic titanium alkoxide TTIP (titanium tetraisopropoxide; JUNSEI; a solid content of 97%) was used.

240 ml of 70% nitric acid was added to 8.94 liters of deionized water to prepare a mixed solution.

The mixed solution was slowly added dropwise to the TTIP, and then stirred under reflux at 80° C. so as to be hydrolyzed.

After completion of the hydrolytic reaction, a blue colloidal solution of titanium dioxide having a solid content of 2.0 wt % and a pH of 0.7 was obtained.

The crystal structure of the colloidal titanium dioxide nanoparticles was found to be the anatase form as observed by XRD, and more than 95% of the colloidal titanium dioxide nanoparticles were present in the particle size range of 15-25 nm.

The colloidal titanium dioxide solution was diluted with 7990 liters to a titanium dioxide concentration of 25 ppm, thereby preparing a liquid composition for promoting plant growth according to the present invention.

Test Example 1

Dispersion Stability Test

In order to determine the dispersion stability of the composition prepared in Example 1, the Zeta-potential of the composition was measured.

It is generally difficult to directly measure the surface potential of colloidal particles and the like, and information on the surface potential is generally discussed by Zeta-potential obtained mainly by an electrophoresis experiment.

In the case of fine particles or colloidal particles, as the absolute value of experimentally determined Zeta potential increases, the repulsive power between the particles become stronger, leading to an increase in the stability of the particles.

Conversely, as the Zeta-potential is closer to zero, the particles are more likely to agglomerate.

Therefore, the Zeta-potential is used as an index of the dispersion stability of colloidal particles.

1. Test Method

1) Measurement Instrument

Zeta-potential was measured using ELS-8000 (Electrophoretic Light Scattering Spectrophotpmater (OTSUKA ELECTRONICS); Model ELS-8000).

2) Test Method and Considerations

Control groups A, B and C which has an initial pH of colloidal titanium dioxide of 2 were pH adjusted with 0.05N NaOH, thus preparing compositions having pH values of 3, 5, 7, 9 and 11, respectively.

As a test group, the composition of Example 1 was prepared. It was pH adjusted with 0.05N NaOH, thus preparing compositions having pH values of 3, 5, 7, 9 and 11, respectively.

2. Test Results

The results of the test are shown in Table 1 below.

TABLE 1

| Sample | PH | Isoelectric point | Zeta-potential(mV) |
|---|---|---|---|
| A | 3.00 | 6.29 | 37.74 |
|  | 5.48 |  | 14.77 |
|  | 7.23 |  | −14.39 |
|  | 9.20 |  | −15.22 |
|  | 11.00 |  | −15.19 |
| B | 3.04 | 3.17 | 1.88 |
|  | 5.54 |  | −25.85 |
|  | 7.27 |  | −27.49 |
|  | 9.15 |  | −29.19 |
|  | 10.99 |  | −28.10 |
| C | 3.01 | 4.11 | 37.65 |
|  | 5.13 |  | −22.61 |
|  | 6.93 |  | −24.00 |

TABLE 1-continued

| Sample | PH | Isoelectric point | Zeta-potential(mV) |
|---|---|---|---|
|  | 9.01 |  | −27.01 |
|  | 11.00 |  | −31.48 |
| Example 1 | 3.00 | — | −17.06 |
|  | 5.01 |  | −27.05 |
|  | 7.13 |  | −24.70 |
|  | 9.03 |  | −27.22 |
|  | 11.00 |  | −29.88 |

Table 1 above shows Zeta-potential values measured at varying pH values. As can be seen in Table 1, the Zeta-potential of the inorganic oxide particles was greatly changed with a change in the pH of the solution.

At a certain pH value, the particles showed an isoelectric point at which the Zeta-potential reached zero.

At the isoelectric point, the particles did not show electrokinetic phenomena such as electrophoresis, and the electrostatic repulsive force of the particles was reduced such that the particles had agglomeration ability.

Thus, obtaining a stable dispersion means that the solution has a pH value different from the isoelectric point of particles.

In order words, as shown in Table 1 above, the samples A, B and C, which were the existing colloidal titanium dioxide particles for photocatalysts, had an isoelectric point.

On the other hand, it can be considered that the composition of Example 1, prepared through surface modification, had dispersion stability, because it had no isoelectric point in absolute value at varying pH values.

Also, it can be seen that the composition of Example 1 had stable Zeta-potential, indicating that it showed dispersion stability for a long period of time. Accordingly, it can be seen that, even when the composition of Example 1 is mixed with a large amount of water after a long period of time, it does not show precipitation, suggesting that it is mostly absorbed by plant foliage when it is applied to plant foliage.

Test Example 2

Measurement of Degree of Absorption of the Inventive Plant Growth Promoting Composition into Plant Foliage In order to confirm whether the composition of the present invention is absorbed into plant foliage, the following test was carried out.

In the test, five kinds of samples were treated with the composition of Example 1, and after 3 days, the leaves of each of the samples were picked. Whether the composition was absorbed into the leaves was analyzed, and the analysis results are shown in Table 2 below.

TABLE 2

|  | Sample 1 | Sample 2 | Sample 3 | Sample 4 | Sample 5 |
|---|---|---|---|---|---|
| Results Example 1 | 15.4 | 14.8 | 3.8 | 4.0 | 4.8 |
| Ultrasonic wave washing | Treated Not washed | Treated Not washed | Treated Washed | Treated Washed | Treated Washed |
| Running water washing | Not washed | Washed | Washed | Not washed | Washed |
| Others |  | Applying the composition of Example 1 to the front side of leaves so as to make the leaves moist |  |  | Applying the composition of Example 1 to the front and back sides of leaves so as to make the leaves moist |

As shown in Table 2 above, 3 days after treatment with the composition of Example 1, the sample 1 subjected to neither ultrasonic wave washing waves nor running water washing contained 15.4 mg/kg of titanium dioxide, and the sample 2 subjected to only running water washing (10 min) without ultrasonic wave washing contained 14.8 mg/kg of titanium dioxide. Also, the sample 4 subjected to ultrasonic wave washing (30 min at 40 KHz) without running water washing contained 4.0 mg/kg of titanium dioxide.

In the case of the measurement carried out after applying the composition only to the front side of the leaves and then completely washing the leaves with ultrasonic waves running water (sample 3), it was seen that 3.8 mg/kg of titanium dioxide was contained in the leaves. In addition, in the case of the measurement carried out after applying the composition to the front and back sides of the leaves and then completely washing the leaves with ultrasonic waves and running water (sample 4), it was seen that a 4.8 mg/kg of titanium dioxide was contained in the leaves.

Such results indicate that about 25% of the composition of Example 1 was absorbed into the leaves.

Because ultrasonic wave washing can remove a portion of already absorbed titanium dioxide, the fact that about 25% of the composition of Example 1 was absorbed after ultrasonic wave washing and running water washing means that a larger amount of titanium dioxide would actually be absorbed.

Test Example 3

Test for Effects of Plant Growth Promoting Composition in Rice Plants

1. Preparation of Test Materials
20 ml of the composition of Example 1 was diluted with water at a ratio of 1:5000 to a total volume of 100 liters (FIG. 1).

20 ml of the composition of Comparative Example 1 was diluted with water at a ratio of 1:5000 to a total volume of 100 liters (FIG. 1).

As a rice variety to be tested, Junambyeo was prepared.

For reference, the degree of precipitation of the compositions of Example 1 and Comparative Example 1 can be seen in FIG. 1.

2. Test Method

A test for each test group was carried out three times using a completely randomized design, and an area of 300 pyung (990 m$^2$) was assigned to each test group.

For comparison, 100 liters of each of the diluted compositions of Example 1 and Comparative Example 1 was applied once to an area of 300 pyung at the booting stage (July 25).

3. Test Results

1) Examination of Growth Period

Rice seeds were sown at the same date, the rice seedlings were transplanted, and then the growth period of the rice was observed.

The observation results are shown in Table 3 below.

TABLE 3

|  | Sowing stage | Transplanting stage | Tillering stage | Panicle formation stage | Booting stage | Heading stage | Ripening stage | Harvesting stage |
|---|---|---|---|---|---|---|---|---|
| Comparative Example 1 | 4.20 | 5.15 | 6.10 | 7.15 | 8.3 | 8.18 | 9.1 | 10.5 |
| Example 1 | 4.20 | 5.15 | 6.10 | 7.15 | 8.3 | 8.15 | 8.28 | 10.5 |

2) Examination of Growth Characteristics

The growth characteristics of the rice plants treated with each of the compositions of Example 1 and Comparative Example 1 for application to plant foliage were examined, and the results are shown in Table 4 below.

TABLE 4

|  | Fresh weight (g/week) | Plant height (cm/week) | Number of effective tillers | Grain weight (g/week) | Fresh weight (g/week) | Plant height (cm/week) | Number of effective tillers | Grain weight (g/week) |
|---|---|---|---|---|---|---|---|---|
|  | Before treatment | | | | 30 days after treatment | | | |
| Comparative Example 1 | 76.5 | 44.3 | — | — | 104.35 | 64.45 | 17.2 | 7.02 |
| Example 1 | 79.2 | 47.1 | — | — | 109.44 | 66.5 | 17.45 | 7.52 |
|  | 45 days after treatment | | | | 70 days after treatment | | | |
| Comparative Example 1 | 128.49 | 73.75 | 20.2 | 27.92 | 147.15 | 75.15 | 19.85 | 33.2 |
| Example 1 | 137.07 | 75.3 | 21.15 | 31.26 | 161.59 | 75.75 | 21.8 | 40.2 |

3) Rice Production and Ripened Grain Ratio

Rice plants were treated with each of the compositions for application to plant foliage, prepared in Example 1 and Comparative Example 1, and grains collected from an area of 1 pyung (3.3 m$^2$) were assorted with brine (specific gravity: 1.06).

Ripened grain ratio was calculated according to the following equation, and the calculation results are shown in Table 5 below:

Ripened grain ratio=perfect grain ratio×100

TABLE 5

|  | Rice production | | Ripened grain ratio |
|---|---|---|---|
|  | Quantity (kg/300 pyung) | Percentage (%) | (based on rice yield) Percentage (%) |
| Comparative Example 1 | 530 | 100 | 85 |
| Example 1 | 656 | 123.7 | 80 |

4) Milling Rate and Component Analysis

Rice grains were milled when the water content reached 14-15%. Then, the measurement of milling rate and the analysis of components were performed, and the results are shown in Table 6 below.

TABLE 6

|  | Milling rate (%) | Ratio (%) |
|---|---|---|
| Comparative Example 1 | 75.2 | 100 |
| Example 1 | 81.4 | 108.2 |

TABLE 7

|  | Components analyzed | | | |
|---|---|---|---|---|
|  | Protein | Amylose | Unit | Analysis method |
| Comparative Example 1 | 7.2 | 19.0 | g/100 g | Analysis of general components before food processing |
| Example 1 | 6.6 | 17.5 | | |

As can be seen in Tables 6 and 7, the composition for application to plant foliage, prepared in Example 1, showed excellent with respect to yield, ripened grain ratio, milling recovery and the like.

Accordingly, it can be seen that, when soil fertility and plant nutrition are insufficient, providing the composition containing titanium dioxide nanoparticles and other components as described in the present invention is preferable in terms of reducing labor and cost and shows an excellent effect of promoting plant growth.

5) Measurement of Amount of Chlorophyll

Each of the composition of Example 1 and the composition of Comparative Example 1 was applied to rice foliage, and the amount of chlorophyll in the rice foliage was measured.

Figure 2:
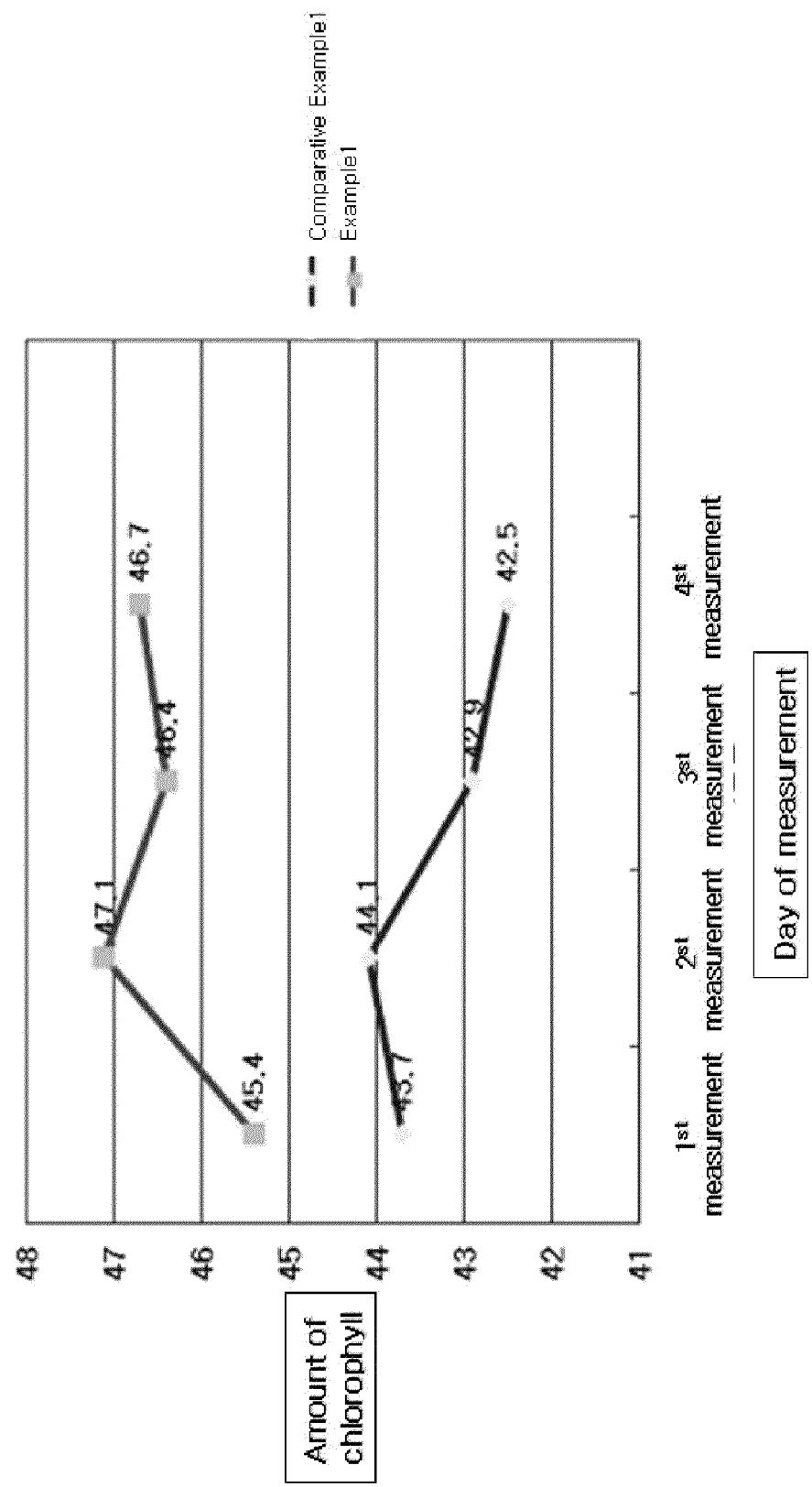
FIG. 2 is a graphic diagram showing the results obtained by applying the inventive composition for promoting plant growth to rice foliage, and then measuring the amount of chlorophyll in the rice foliage.

The measurement results are shown in FIG. 2.

As shown in FIG. 2, the amount of chlorophyll in the group treated with the composition of Comparative Example 1 was decreased with the passage of time, whereas the amount of chlorophyll in the group treated with the composition of Example 1 was continuously increased.

Accordingly, it can be seen that the group treated with the composition of Example 1 was actively photosynthesized through continuous exposure to sunlight, indicating smooth growth, and this active photosynthesis is possible whether or not light conditions are good.

As described above, according to the present invention, there is provided a liquid composition for promoting plant growth, which contains colloidal titanium dioxide which is prevented from rapidly precipitating.

When the inventive composition for promoting plant growth is applied to a plant, a portion of the titanium dioxide is absorbed into the plant to promote the internal photosynthetic mechanism and metabolism, and the non-absorbed portion remains on the surface of the plant and shows the effect of increasing the plant resistance to various external pathogenic bacteria.

What is claimed is:

1. A liquid composition for promoting plant growth containing titanium dioxide nanoparticles, wherein the liquid composition contains, as an active ingredient, an aqueous solution prepared by adjusting the pH of colloidal titanium dioxide, a plant growth promoting component, to 0.4-0.6, in order to prevent rapid precipitation of the colloidal titanium dioxide, and then diluting the colloidal titanium dioxide with water to a predetermined concentration.

2. The liquid composition of claim 1, wherein the pH of the colloidal titanium dioxide is adjusted by adding to the colloidal titanium dioxide an inorganic acid together with one or two selected from the group consisting of an organic acid, having a hydroxyl group (—OH) and a carboxyl group (—COOH), and a carbon-based amino acid having a hydroxyl group (—OH), an amino group (—NH$_2$) and a carboxyl group (—COOH) as polar functional groups.

3. The liquid composition of claim 2, wherein the amino acid is at least one selected from the group consisting of serine and threonine.

4. The liquid composition of claim 2, wherein the organic acid is at least one selected from the group consisting of glycolic acid, lactic acid, citric acid, tartaric acid, malic acid and gluconic acid.

5. The liquid composition of claim 2, wherein the inorganic acid is at least one selected from the group consisting of hydrogen chloride, hydrogen bromide, hydrogen iodide, nitric acid, sulfuric acid and perchloric acid.

6. The liquid composition of claim 1, wherein the aqueous solution further contains at least alkaline substance selected from the group consisting of alkali metal hydroxides, including sodium hydroxide (NaOH), potassium hydroxide (KOH) and lithium hydroxide (LiOH), ammonium hydroxide (NH$_4$OH), trimethylamine ((CH$_3$)$_3$N) and triethylamine ((C$_2$H$_5$)$_3$N).

7. The liquid composition of claim 1, wherein the aqueous solution further contains at least one selected from the group consisting of assistant additives necessary for plant growth and surfactants for dispersion.

8. The liquid composition of claim 1, wherein the aqueous solution is adjusted to a carbon dioxide concentration of 1-1,000 ppm.

9. A method for preparing a liquid composition for promoting plant growth containing titanium dioxide nanoparticles, the method comprising the steps of:
adjusting the pH of colloidal titanium dioxide, a plant growth promoting component, to 0.4-0.6, in order to prevent rapid precipitation of the colloidal titanium dioxide; and then
diluting the colloidal titanium dioxide with water to a predetermined concentration, thereby preparing an aqueous solution.

10. The method of claim 9, wherein the pH of the colloidal titanium dioxide is adjusted by further adding thereto an inorganic acid and one or two selected from the group consisting of an organic acid, having a hydroxyl group (—OH) and a carboxyl group (—COOH), and a carbon-based amino acid having a hydroxyl group (—OH), an amino group (—NH$_2$) and a carboxyl group (—COOH) as polar functional groups.

11. The method of claim 9, wherein the aqueous solution is neutralized by further adding thereto at least one alkaline substance selected from the group consisting of alkali metal hydroxides, including sodium hydroxide (NaOH), potassium hydroxide (KOH) and lithium hydroxide (LiOH), ammonium hydroxide (NH$_4$OH), trimethylamine ((CH$_3$)$_3$N) and triethylamine ((C$_2$H$_5$)$_3$N).

12. The method of claim 9, wherein at least one selected from the group consisting of assistant additives necessary for plant growth and surfactants for dispersion is further added to the aqueous solution.

* * * * *